(12) United States Patent
Fuhrherr et al.

(10) Patent No.: US 11,464,834 B2
(45) Date of Patent: Oct. 11, 2022

(54) ORODISPERSIBLE TABLET CONTAINING BURLULIPASE AND PHARMACEUTICAL COMPOSITION PRODUCED THEREFROM

(71) Applicant: Nordmark Pharma GmbH, Uetersen (DE)

(72) Inventors: Richard Fuhrherr, Uetersen (DE); Jan Lüdemann, Uetersen (DE); Lisa Garrett, Wiltshire (GB)

(73) Assignee: Nordmark Pharma GmbH, Uetersen (DE)

( * ) Notice: Subject to any disclaimer, the term of this patent is extended or adjusted under 35 U.S.C. 154(b) by 152 days.

(21) Appl. No.: 16/490,549

(22) PCT Filed: Mar. 5, 2018

(86) PCT No.: PCT/EP2018/055285
§ 371 (c)(1),
(2) Date: Sep. 1, 2019

(87) PCT Pub. No.: WO2018/158459
PCT Pub. Date: Sep. 7, 2018

(65) Prior Publication Data
US 2020/0009232 A1 Jan. 9, 2020

(30) Foreign Application Priority Data
Mar. 3, 2017 (DE) ...................... 10 2017 104 472.8

(51) Int. Cl.
| | | |
|---|---|---|
| *A61K 38/46* | (2006.01) |
| *A61K 9/00* | (2006.01) |
| *A61K 9/08* | (2006.01) |
| *A61K 9/19* | (2006.01) |
| *A61K 47/02* | (2006.01) |
| *A61K 47/10* | (2017.01) |
| *A61K 47/42* | (2017.01) |

(52) U.S. Cl.
CPC .......... *A61K 38/465* (2013.01); *A61K 9/0056* (2013.01); *A61K 9/0095* (2013.01); *A61K 9/08* (2013.01); *A61K 9/19* (2013.01); *A61K 47/02* (2013.01); *A61K 47/10* (2013.01); *A61K 47/42* (2013.01); *C12Y 301/01003* (2013.01)

(58) Field of Classification Search
CPC ...... A61K 38/465; A61K 9/0056; A61K 9/08; A61K 9/19; A61K 47/02; C12Y 301/01003
See application file for complete search history.

(56) References Cited

U.S. PATENT DOCUMENTS

| | | | |
|---|---|---|---|
| 6,740,339 B1 | 5/2004 | Ohkouchi et al. | |
| 7,718,169 B2 * | 5/2010 | Margolin | A61K 38/48 424/94.2 |
| 2011/0293590 A1 * | 12/2011 | Ramsch | A61P 1/00 424/94.3 |

FOREIGN PATENT DOCUMENTS

| | | |
|---|---|---|
| CN | 1394607 A | 2/2003 |
| CN | 101068565 A | 11/2007 |
| CN | 104109662 A | 10/2014 |
| DE | 2638088 A1 | 3/1978 |
| DE | 102009006594 A1 | 8/2010 |
| DE | 102015114857 A1 | 3/2017 |
| EP | 2786761 A1 | 1/2009 |
| JP | 2006502972 A | 1/2006 |
| WO | 0061117 | 10/2000 |
| WO | 2005092370 A1 | 10/2005 |
| WO | 2006044529 A1 | 4/2006 |
| WO | 2010085975 A1 | 1/2009 |
| WO | 2010025126 A1 | 3/2010 |
| WO | 2014166994 A1 | 10/2014 |

OTHER PUBLICATIONS

Heubi et al. Safety and Efficacy of a Novel Microbial Lipase in Patients with Exocrine Pancreatic Insufficiency due to Cystic Fibrosis: A Randomized Controlled Clinical Trial. J Pediatr. 2016;176:156-61.*
NursingTimes. The administration of medicines. Drugs (Drugs. 2017; 1-8. Nursing Times. 2007;1-8.*
Boran et al. Chapter 5—Fish Gelatin. Adv Food Nutr Res. 2010;60:119-43.*
Sadikoglu et al. Freeze-Drying of Pharmaceutical Products: Research and Development Needs. Drying Technology. 2006;24:849-861.*
Drugs. Inactive Ingredients. Drugs. 2017;1-8.*
Corresponding Chinese Patent Application 201880019225.8 Office Action dated Apr. 29, 2021.
Corresponding Chinese Patent Application 201880019225.8 Office Action dated Dec. 15, 2021.
Corresponding German Search Report dated Oct. 10, 2017.
Corresponding PCT Application PCT/EP2018/055285 International Search Report dated May 23, 2018.
Corresponding Japanese Patent Application 2019-547658 Office Action dated May 3, 2018.
Acta Pharm; 61 (2011) 117-139; The Technologies Used for Developing Orally Disintegrating Tablets: A Review.

(Continued)

*Primary Examiner* — Lynn Y Fan
(74) *Attorney, Agent, or Firm* — Grogan, Tuccillo & Vanderleeden LLP

(57) ABSTRACT

The present invention relates to an orodispersible tablet characterized in that it includes burlulipase. It also relates to liquid pharmaceutical compositions that contain solutions of such orodispersible tablets in water or other beverages. It relates to drugs that contain or consist of such orodispersible tablets or solutions. In particular, it relates to such drugs that are suitable for treating digestive problems, in particular exocrine pancreatic insufficiency used to treat digestive problems. In particular, they are for the treatment of exocrine pancreatic insufficiency in cystic fibrosis patients and for treatment of exocrine pancreatic insufficiency in pediatric patients.

16 Claims, No Drawings

(56) References Cited

OTHER PUBLICATIONS

Acta Pharm; The Physical Characteristics of Lyophilized Tablets Containing a Model, Drug in Different Chemical Forms and Concentrations.
Internal Journal of Pharmaceutics; 435 (2012) 131-151; 2019-547658.
ClinicalTrials.gov; Efficacy and Tolerability of NM-BL in Patients With Exocrine Pancreatic Nsufficiency Due to Cystic Fibrosis.
European Journal of Pharmaceutics and Biopharmaceutics; 78 (2011) 462-469; Orally Disintegrating Mini-Tablets (ODMTS); A Novel Solid Oral Dosage Form for Paediatric Use.
www.jpeds.com; The Journal of Pediatrics; Safety and Efficacy of a Novel Microbial Lipase in Patients With Exocrine Pancreatic Insufficiency Due to Cystis Fibrosis: A Randomized Controlled Clinical Trial.
English translation of corresponding Japanese Application No. 2019-5476 58 Office Action dated May 18, 2021.
Ref. 3 in attached corresponding JP Office Action; M. Yoneko, Development of pediatric formulations in foreign guidelines, Pharmacy, 2013, vol. 64, No. 10, p. 2619-2623 (document showing well-known technology).
Ref. 5 in attached corresponding JP Office Action; Kumiko Isaka and Osamu Kumasaka, Pediatric Dosage Forms and Adherence to Medication: OD and Chewable Tablets for Pediatric Use, Pharmacy, 2013, vol. 64, No. 10, p. 2641-2649 (reference indicating known technology).

* cited by examiner

ORODISPERSIBLE TABLET CONTAINING BURLULIPASE AND PHARMACEUTICAL COMPOSITION PRODUCED THEREFROM

The present invention relates to an orodispersible tablet, which is characterized in that it comprises burlulipase. It further relates to liquid pharmaceutical compositions containing solutions of such orodispersible tablets in water or other beverages. It relates to pharmaceutical products containing or consisting of such orodispersible tablets or solutions. In particular, it relates to such pharmaceutical products which are suitable for the treatment of digestive problems, in particular exocrine pancreatic insufficiency. In particular, they are suitable for the treatment of exocrine pancreatic insufficiency in patients having mucoviscidosis and for the treatment of exocrine pancreatic insufficiency of patients in pediatrics.

PRIOR ART

Exocrine pancreatic insufficiency is a disease in which insufficient formation of pancreatic enzymes occurs, as a result of which the food can no longer be adequately digested. This disease can be contracted, for example, by loss of pancreatic tissue in chronic pancreatitis or by pancreatic cancer, but can also be congenital due to genetically related diseases, such as mucoviscidosis. Exocrine pancreatic insufficiency leads to various digestive problems, such as steatorrhea (fatty stool), and is normally treated by administration of digestive enzymes with the meals (enzyme replacement therapy).

Mucoviscidosis is an autosomal recessive inherited metabolic disorder, in which the composition of all secretions of exocrine glands is altered. In that, the salt and water transport of the cells is disturbed and, inter alia, the digestive juices formed by the pancreas are more viscous than normal and clog the excretory ducts of the gland. The accumulating digestive juices lead to irritation and finally to damage to the pancreas.

In the case of enzyme substitution, a product obtained from pancreases of pigs is administered perorally in the form of so-called "pancreatin". Pancreatin is a solid produced in a multistage process, which comprises the degreasing of pancreases of pigs and the removal of fibers therefrom. It is a brown powder, which, in addition to the desired main constituents lipase, protease and amylase, also contains a large number of residues from the pancreases of pigs. In the European Pharmacopoeia (Ph. Eur.), pancreatin is described as "pancreatic powder" (pancreas powder) and in the United States Pharmacopoeia (USP) as "pancreatin" or "pancrelipase". Generally available forms of administration for pancreatin are coated tablets, micro-tablets, micro-dragées, capsules, powders and granules or pellets, resp., preferably with a gastric juice-resistant film coating, since the pancreatic enzymes, in particular pancreatin lipase, are unstable in acidic gastric juice.

The treatment with pancreatin, however, has disadvantages. On the one hand, pancreatin contains large proportions of non-active components from the pancreas. Therefore, the activity is relatively low and large amounts of pancreatin must be taken in order to achieve effective therapy. Depending on the formulation, a large number of capsules or tablets must be taken; in individual cases, these can be up to 8-15 tablets or capsules per meal. This is unpleasant and often leads to compliance problems. On the other hand, the pancreatin contains varying amounts of viral and microbial impurities originating from the pancreas of the pigs. In view of the discussion about bovine spongiform encephalopathy, biological impurities originating from mammals in pharmaceutical products are seen increasingly critical by the approval authorities. Therefore, approvals of pharmaceutical products produced from animal tissue are increasingly problematic. Even more problematic is the administration of pancreatin to infants and young children. Normally, these cannot swallow capsules. Therefore, the capsules containing, for example, pancreatic enzyme preparations are opened and the solid, gastric juice-resistantly coated multi-particulate units contained therein are distributed on or in the food. In case of such peroral intake, the integrity of the functional gastric juice-resistant coating can be destroyed by chewing and the enzymes can be released in the wrong place, in particular before the gastric passage, denatured and thus rendered ineffective. In addition, pancreatin cannot be administered in the liquid form, which likewise represents an obstacle for use in pediatrics.

Furthermore, the proteases and amylases, which are always present in pancreatin products, are undesirable in some treatments: the amylase content is undesirable for children having mucoviscidosis and proteases are contraindicated in patients with acute pancreatitis or active phases of chronic pancreatitis (see U.S. Pat. No. 5,645,832). Therefore, the availability of a lipase as a single protein would be advantageous.

The use of lipases other than pancreatic lipase has been proposed many times. In particular, microbiologically produced lipases have been disclosed for this purpose. DE 1 642 654 A1 discloses the preparation of a lipase by fermentation of the fungal species *Rhizopus arrhizus* and recovery of the lipase from the mother liquor. Use of the lipase as a pharmaceutical product for the treatment of pancreatic insufficiencies and similar diseases is likewise proposed. EP 387 945 A describes the use of the same lipase in combination with pancreatin for the treatment of pancreatic insufficiencies. U.S. Pat. Nos. 5,489,530 and 5,645,832 disclose bacterial lipases and consider their use as pharmaceutical products for the treatment of pancreatic insufficiencies.

US 2006/121017 A1 discloses compositions containing bacterial lipase, protease and amylase. The lipase can be derived from the genus *Pseudomonas* or *Burkholderia* or from the species *Burkholderia cepacia*. WO 2010/025126 A1 discloses rapidly disintegrating tablets with the same ingredients, which additionally contain an effervescent additive. The tablets rapidly dissolve in the oral cavity. The stabilization of the lipases is provided by crystallization or cross-linking.

The use of cross-linked lipase crystals of lipases from the genus *Burkholderia* in mixtures with a certain protease and a certain amylase is disclosed.

Finally, WO 2010/085975 A1 discloses liquid forms of preparation of burlulipase for the treatment of digestive disorders, in particular pancreatitis and mucoviscidosis. The lipase is obtained from the genus *Burkholderia*, the genus *Pseudomonas* or from the species *Burkholderia plantarii* by fermentation and recovery of the lipases from the culture supernatant.

However, burlulipase has disadvantages, which have hitherto prevented its practical use in pharmaceutical products. It is thermally unstable in liquid solutions, and therefore such solutions cannot be stored at room temperature, which is disadvantageous. The preparation of tablets and granules is normally accompanied by a considerable loss of activity (unpublished data). In the tableting process, 20 to 70% of the burlulipase are usually inactivated. This not only leads to a reduction of the lipase activity, but also to an unacceptable deviation of the active ingredient content in various batches.

In contrast to pancreatin, with burlulipase it is possible to provide pharmaceutical products with only one single digestive enzyme. Furthermore, the specific activity of burlulipase is very high, so that only small amounts of substance have to be administered. The pH range for the stability and activity of burlulipase is between pH 4 and pH 9 and therefore overcomes the restrictions on stability and activity of porcine lipase or porcine pancreatin, resp., which are deactivated in the stomach. For limited periods of time, burlulipase can also withstand stresses at pH values well below pH 4. This means that the lipolytic effect of the bacterial lipases can be applied in the gastrointestinal tract with a greater effect than is the case with products for the therapy of digestive disorders common on the market. The fact that burlulipase, contrary to pancreatin, is largely stable at the pH value of gastric juice for a certain period of time, makes it seem suitable for the production of perorally administered forms of preparation.

OBJECT OF THE PRESENT INVENTION

The object of the present invention is to provide a pharmaceutical product containing burlulipase. This pharmaceutical product is intended to solve or alleviate the above-mentioned problems of burlulipase. In particular, the pharmaceutical product should be producible without a high loss of activity. Furthermore, it is an object of the present invention to provide a pharmaceutical product which can be stored without a high loss of activity. In addition, the pharmaceutical product should be producible in precisely defined doses. Furthermore, a process is to be provided which enables producing such a pharmaceutical product without the activity of the burlulipase used greatly decreasing during the production process. In addition, the pharmaceutical product should enable the preparation of liquid forms of preparation of the burlulipase, in which the activity of the burlulipase, compared to the activity of the burlulipase originally used to prepare the pharmaceutical product, is reduced only slightly or not at all. The pharmaceutical product is intended to enable the administration of burlulipase in liquid forms of preparation. It is therefore also an object of the present invention to provide a liquid pharmaceutical composition, which may be used in pediatrics and/or which is suitable for the treatment of mucoviscidosis and/or for tube administration in artificial feeding.

DESCRIPTION OF THE INVENTION

Orodispersible Tablets

One aspect of the present invention is an orodispersible tablet, which is characterized in that it contains burlulipase. Burlulipase (International Nonproprietary Name, INN) is the lipase of the bacterial species *Burkholderia plantarii*. Burlulipase is a triacylglycerol hydrolase (EC 3.1.1.3), which has a amino acid sequence corresponding with the lipases produced by *Burkholderia plantarii* and *Burkholderia glumae*. Burlulipase is produced by a classical fermentation process, in which *Burkholderia plantarii*, a non-recombinant Gram-negative bacterium, is used as a production strain. Pure burlulipase can have a specific activity of more than 3,500 u/mg (tributyrin units per milligram of protein). On account of this high lipolytic activity, burlulipase is particularly suitable for assisting the digestive performance in healthy and diseased humans. Burlulipase can be obtained in very high concentrations with high activity, so that only small amounts of substance (i.e. a small mass or a small volume of solution, resp.) have to be administered. The suitability of liquid preparations of burlulipase for the treatment of digestive disorders is known from WO 2010/085975 A1.

The preparation of solid forms of preparation of burlulipase is normally accompanied by a high loss of the activity of burlulipase. Typically, only about 60% of the original activity of the burlulipase used remains in the tablets. The degree of activity loss also depends on the process conditions. At the same time, burlulipase appears to be sensitive to some of the excipients used in tablets. Surprisingly, however, it could be demonstrated that it is possible to produce orodispersible tablets containing burlulipase, the production of which is possible virtually without loss of the activity of burlulipase. The orodispersible tablets can be easily produced and allow storage at room temperature over a period of time common for pharmaceutical products. Even upon storage for several years, the activity of the burlulipase contained therein decreases only to a pharmaceutically acceptable degree.

In addition, the orodispersible tablets according to the invention allow the simple and rapid preparation of solutions, emulsions or suspensions by simply combining the orodispersible tablets with a liquid such as, for example, water, beverages or the like, optionally with stirring. Therefore, orodispersible tablets allow the provision of liquid pharmaceutical products without having to cool the preparation during storage. On the other hand, liquid forms of preparation of burlulipase are thermally unstable and can only be marketed in the form of cooled solutions, with all the problems involved in an uninterrupted cooling chain. Here, orodispersible tablets can be successfully used to avoid the storage of liquid forms of preparation. The packaging, too, is simpler than in the case of liquids.

According to the European Pharmacopoeia, $8^{th}$ Edition (Ph. Eur.), Volume 1—general part, monographic groups, a disintegration time (in water) of max. three minutes is required for orodispersible tablets. The orodispersible tablets described here dissolve in water at 20° C. in less than 2 minutes. When stirred, however, they are usually dissolved within a few seconds, typically in less than 10 seconds, usually in 2 to 5 seconds.

It is preferred that the orodispersible tablet as described herein contains a lyophilizate. Particularly preferably it contains a lyophilizate of a composition containing burlulipase. Such lyophilizates can be prepared from solutions, emulsions or suspensions of burlulipase, e.g., by freeze-drying. Alternative preparation processes are, for example, spray drying, vacuum drying or spray freeze-drying. With freeze-drying and spray freeze-drying, the preparation can be carried out gently at low temperatures. The lyophilizates are preferably prepared from solutions. Solutions give very homogeneous and highly porous lyophilizates, which dissolve rapidly in liquids. Particularly preferred is an orodispersible tablet according to the invention, which contains a lyophilizate of an aqueous solution of burlulipase. Such solutions produce lyophilizates, in which the active ingredient is very homogeneously distributed. Furthermore, the temperature during freeze-drying is preferably 0° C. or less. At such temperatures, the burlulipase is stable. It is especially preferred if the orodispersible tablet according to the invention contains a lyophilizate of an aqueous solution of burlulipase, which has been freeze-dried at a temperature of 0° C. or less. The solutions, emulsions or suspensions of burlulipase are most preferably cooled by means of liquid air before being freeze-dried. Rapid cooling leads to a homogeneous frozen mass. In the freeze-drying process, less excipients are used than upon pressing of a classical tablet, and the necessary excipients do not act on or hardly act on burlulipase in an inactivating manner.

Most preferred is the use of solutions of burlulipase for the preparation of the lyophilizate, such as are formed after expression of the burlulipase and treatment of the culture supernatant. These solutions may then be mixed with excipients and lyophilized. Particularly preferably the orodispersible tablet consists of a lyophilizate as described herein.

In the production of the orodispersible tablets according to the invention, the burlulipase surprisingly is not or hardly inactivated. Furthermore, the orodispersible tablets are surprisingly stable upon storage at room temperature. Therefore, artificial stabilization of the burlulipase can be dispensed with. The use of crystalline burlulipase becomes unnecessary. It is also not necessary to cross-link the burlulipase. Both are proposed in the literature for stabilizing lipases (see, e.g., WO 1010/025126, paragraph [033]). Crystallization, however, is a complicated, not easily reproducible process and cross-linking is likewise complex and usually results in a partial inactivation of the burlulipase. Therefore, the orodispersible tablet according to the invention is preferably characterized in that the burlulipase contained therein is not chemically modified. It is furthermore preferably characterized in that the burlulipase contained therein is not present in a crystalline form, i.e. is amorphous. Particularly preferably, the burlulipase is not chemically modified and is present in an amorphous form. The orodispersible tablet according to the invention preferably contains 0.01% by weight to 90% by weight of burlulipase, more preferably 0.1% by weight to 40% by weight, particularly preferably 1% by weight to 30% by weight, and most preferably 2% by weight to 20% by weight. Unless indicated otherwise, all percentages given in this text refer to the total mass of the orodispersible tablet without the residual water content as determined according to Karl Fischer.

Since burlulipase can be inactivated by the action of pressure, increased pressures should be avoided as far as possible. Therefore, for the orodispersible tablets according to the invention, production processes according to the invention are preferred, in which pressing processes are dispensed with. Particularly preferred for the orodispersible tablets according to the invention are production processes according to the invention, in which any mechanical pressure impact for compacting or consolidating the orodispersible tablets is dispensed with.

In addition to burlulipase, the orodispersible tablets according to the invention also contain excipients. Excipients in terms of this application are all adjuvants which are customarily used in pharmaceutical compositions. Active substances, in particular enzymes, are not excipients in terms of this application. Excipients are listed, for example, in the "Handbook of Pharmaceutical Excipients" of the "American Pharmaceutical Association". Excipients particularly suitable for the orodispersible tablets according to the invention are listed, for example, in paragraph [0019] of EP 1 804 764 B1. The orodispersible tablet according to the invention preferably contains 10% by weight to 99.99% by weight of excipients, more preferably 60% by weight to 99.9% by weight, particularly preferably 70% by weight to 99% by weight, and most preferably 80% by weight to 98% by weight.

The orodispersible tablet according to the invention preferably contains at least one binder in addition to the burlulipase. In principle, all known binders are suitable. Preferably, however, the binder is selected from the group consisting of gelatin, hydrolyzed gelatin, polyvinyl pyrrolidone, e.g., Kollidon®, cellulose ether and pregelatinized starch. Gelatin is particularly preferred, and fish gelatin is most preferred. In particular it can be unaltered natural fish gelatin, non-gelling fish gelatin, hydrolyzed fish gelatin or spray-dried fish gelatin. The binders can be present in the amounts given above for the excipients. Preferably, the orodispersible tablet according to the invention contains at least one excipient selected from the group consisting of binders and structure-forming excipients.

In principle, all known fillers and structure-forming excipients are suitable. Preferably, these are selected from the group consisting of sugar alcohols, sugars, cellulose powder, calcium sulfate and microcrystalline cellulose. Sugar alcohols and sugars are preferred, and mannitol is most preferred. The structure-forming excipients can be present in the amounts given above for the excipients.

The orodispersible tablet according to the invention preferably contains 0.01% by weight—90% by weight of burlulipase, 5% by weight—90% by weight of binder and 5% by weight—90% by weight of structure—forming excipients. More preferably, the orodispersible tablet according to the invention contains 0.1% by weight—40% by weight of burlulipase, 20% by weight—80% by weight of binder and 20% by weight—80% by weight of structure—forming excipients. Particularly preferably, the orodispersible tablet according to the invention contains 1% by weight—30% by weight of burlulipase, 25% by weight—55% by weight of binder and 20% by weight—50% by weight of structure—forming excipients. Most preferably, the orodispersible tablet according to the invention contains 2% by weight—20% by weight of burlulipase, 30% by weight—50% by weight of binder and 25% by weight—45% by weight of structure-forming excipients.

Furthermore, the orodispersible tablet according to the invention can contain excipients which are selected from the group consisting of preservatives, stabilizers, wetting agents, emulsifiers, dissolving aids, salts for regulating osmotic pressure, disintegrants, effervescent additives and pH buffers. The orodispersible tablet according to the invention preferably contains or consists of burlulipase, binders, structure-forming excipients, emulsifiers and optionally an acid or base for adjusting the pH value. More preferably, the orodispersible tablet according to the invention contains or consists of burlulipase, binders, structure-forming excipients and optionally an acid or base for adjusting the pH and/or a surfactant for improving the disintegration or the dissolution behavior. Most preferably, the orodispersible tablet according to the invention contains or consists of burlulipase, fish gelatin, mannitol and sodium hydroxide. Also particularly preferably, the orodispersible tablets according to the invention consist of burlulipase, fish gelatin, mannitol and citric acid. Also particularly preferably, the orodispersible tablets according to the invention consist of burlulipase, fish gelatin, mannitol and poloxamer. Also particularly preferably, the orodispersible tablets according to the invention consist of burlulipase, fish gelatin, mannitol and polysorbate.

In addition to all other ingredients, the orodispersible tablet according to the invention disclosed herein may also contain residual amounts of water. The amount of residual water in the orodispersible tablet preferably is 10% by weight or less, more preferably 7% by weight or less and most preferably 5% by weight or less. Furthermore, it is preferred that the amount of residual water is in the range from 0.1 to 10% by weight, preferably in the range from 0.5 to 6% by weight, and more preferably in the range from 1 to 5% by weight. The amounts of residual water respectively refer to the total mass of the orodispersible tablet.

Preference is also given to orodispersible tablets according to the invention, which contain burlulipase, fish gelatin, mannitol, sodium hydroxide and residual amounts of water. Especially preferred are orodispersible tablets according to the invention, which consist of burlulipase, fish gelatin, mannitol, sodium hydroxide and residual amounts of water. If an acid or base is used for adjusting the pH value, then the statement that the orodispersible tablet contains this acid or base shall also relate to the state in which part of the acid or base is neutralized by other constituents of the orodispersible tablet and is thus present in the form of the salts thereof.

The preferred excipients do not or do not substantially impair the stability of the burlulipase during the storage of the orodispersible tablets. The same applies to the liquid compositions, which are freeze-dried, during freeze-drying and to the liquid compositions, when they are prepared for freeze-drying. These, however, cannot be stored at more than about 10° C. for a prolonged period of time and need to be cooled, if necessary, since otherwise they are partially inactivated. However, normally this is not attributable to the influence of the excipients stated. This rather is a property of the burlulipase.

Furthermore, the orodispersible tablets according to the invention may contain stabilizers. These can be such stabilizers, which stabilize the burlulipase in the orodispersible tablets themselves. Furthermore, these can also be such stabilizers, which stabilize the burlulipase in the liquid compositions used to prepare the orodispersible tablets by freeze-drying. These can also be such stabilizers, which stabilize the burlulipase in the liquid pharmaceutical products produced from the orodispersible tablets by dissolving, emulsifying or suspending them (see further below). Finally, these can also be such stabilizers, which stabilize the burlulipase in the body after ingestion and in particular in the gastrointestinal tract. The stabilizers are preferably selected from the group consisting of salts, organic acids, amino acids, detergents, sugars, oils or viscosity regulators. Particularly preferred is an orodispersible tablet according to the invention, which contains calcium chloride as a stabilizer.

In addition to burlulipase, the orodispersible tablet according to the invention can contain other active ingredients.

Burlulipase is sensitive to some effervescent additives and disintegrants. The burlulipase can be inactivated as a consequence of high-energy interfacial phenomena at the interface of the gas bubbles resulting from an effervescent additive. Therefore, an orodispersible tablet preferably is as described herein, which contains no effervescent additive. Also preferred is an orodispersible tablet, which contains no disintegrants. Most preferred is an orodispersible tablet containing neither an effervescent additive nor disintegrants.

The orodispersible tablet as described herein preferably contains (for example for a 200 µl blister) 0.1 to 20 mg of burlulipase protein, more preferably it contains 0.5 to 10 mg and particularly preferably 1 to 5 mg. An orodispersible tablet with an analogous formulation contains, for example in a 1200 µl blister, e.g. particularly preferably between 5 and 25 mg of burlulipase protein. In that, the amount of burlulipase depends, of course, on the activity thereof and the dosage required for a particular treatment. It is therefore also possible to use amounts of less than 0.1 mg or amounts of more than 20 mg of burlulipase protein.

The orodispersible tablet according to the invention as described herein can contain other enzymes in addition to the burlulipase, in particular other digestive enzymes. In particular, enzymes selected from the group consisting of proteases and amylases come into consideration as digestive enzymes. The present invention also concerns orodispersible tablets containing both protease and amylase. However, orodispersible tablets which contain no further enzymes are preferred. Such pharmaceutical forms are suitable for the treatment of diseases, in which the presence of other enzymes, such as proteases and amylases, is undesirable. For example, proteases are contraindicated in acute pancreatitis or active phases of chronic pancreatitis. Amylases are particularly disadvantageous in mucoviscidosis.

Liquid Pharmaceutical Composition Produced from Orodispersible Tablets

A further aspect of the present invention is a liquid pharmaceutical composition comprising burlulipase, characterized in that it is prepared by introducing an orodispersible tablet according to the invention as described herein into a liquid. The orodispersible tablets are thus produced and taken according to the same method as in the case of using Alka-Seltzer®. A liquid pharmaceutical composition of this type has the advantage that it can be easily administered, even and in particular to children. The liquid pharmaceutical composition according to the invention offers the possibility of convenient dosing of the pharmaceutical product, the homogeneous distribution of the burlulipase in food and the possibility of application in artificial feeding (tube administration). The liquid pharmaceutical composition according to the invention is preferably prepared by introducing an orodispersible tablet according to the invention into a beverage. The beverage can be, for example, water, fruit juice, such as orange juice, milk or the like. The liquid pharmaceutical composition according to the invention can be a solution, a suspension or an emulsion. A solution is preferred. Aqueous solutions are most preferred, and among these, solutions in drinking water are preferred.

In the liquid pharmaceutical composition, burlulipase is preferably present in a concentration of 0.0002 mg/ml to 50 mg/ml, more preferably in a concentration of 0.002 mg/ml to 5 mg/ml and particularly preferably in a concentration of 0.001 mg/ml to 2 mg/ml. In the case of burlulipase, this data is based on the burlulipase protein. Burlulipase is normally present in association with sugars (e.g., 6-deoxy-talane), which, however, are not to be considered in the determination of the burlulipase content. This shall apply to all quantities given with respect to burlulipase in this text.

The orodispersible tablets according to the invention can of course also be administered as such perorally and then dissolve in the oral cavity within a very short time. However, administration as a liquid pharmaceutical composition according to the invention is preferred. Only the orodispersible tablets according to the invention enable the provision of liquid pharmaceutical compositions containing burlulipase, since they solve three problems, which hitherto hampered a broad use of burlulipase as a pharmaceutical product. They can be prepared easily and without great losses of the activity of burlulipase. They can be stored for long periods of time without a high loss of the activity of burlulipase, and they can be converted into liquid pharmaceutical forms with simple means within seconds directly before the ingestion. This also takes place virtually without loss of activity.

The liquid pharmaceutical composition according to the invention preferably is a pharmaceutical product for preventing and/or treating digestive problems or for preventing and/or treating diseases, in which digestive problems play a role. Preferably, drinking the beverage is started after the meal has begun, preferably after approximately ¼ of the meal has been consumed.

Process for Producing the Orodispersible Tablets

A further aspect of the present invention is a process for producing an orodispersible tablet according to the invention as described herein, comprising the steps of:
- providing an aqueous solution, emulsion or suspension containing the burlulipase and excipients,
- filling the aqueous solution, emulsion or suspension into a mold,
- freezing the aqueous solution, emulsion or suspension in the mold,
- freeze-drying the aqueous solution, emulsion or suspension in the mold.

The rate of recovery of the activity of burlulipase in the orodispersible tablet compared to the solution, emulsion or suspension used to prepare the lyophilizate is usually more than 90%. The above-mentioned process is preferred, in which at least 90%, more preferably 95% and most preferably 98% of the activity of burlulipase in the aqueous solution, emulsion or suspension used in the production of the orodispersible tablet is recovered in the orodispersible tablet. A solution is preferably used.

For carrying out this process, all solutions, emulsions or suspensions described herein for the production of the orodispersible tablets according to the invention are suitable. Furthermore, these solutions, emulsions or suspensions can contain all ingredients, in particular excipients, described for the orodispersible tablet. Furthermore, all process steps and process conditions described herein can be used without restriction for freezing and freeze-drying. As a form, a blister is preferably used, which is intended for freeze-drying. Such blisters are described, for example, in US 2002/112449 A.

Pharmaceutical Product

A further aspect of the present invention is a pharmaceutical product for preventing or treating lipase insufficiency comprising an orodispersible tablet according to the invention or a liquid pharmaceutical product according to the invention. Preferably, it is a pharmaceutical product for preventing or treating digestive problems in adults, young children and infants. Preferably it is a pharmaceutical product for the treatment of young children and infants. Also preferably it is a pharmaceutical product for the treatment of digestive disorders, in particular as a consequence of pancreatitis, and digestive disorders, which occur in mucoviscidosis. Particularly preferably, it is a pharmaceutical product for the prevention and/or treatment of pancreatic diseases such as pancreatitis, in particular exocrine pancreatic insufficiency, and pancreatic diseases associated with mucoviscidosis, such as pancreatitis, in particular exocrine pancreatic insufficiency.

EXAMPLES

Reagents/Excipients

Avicel® PH-101: microcrystalline cellulose of the company FMC;

Emcompress: calcium hydrogen phosphate dihydrate of the company JRS Pharma, Rosenberg, Germany;

Kollidon® CL: polyvinylpyrrolidone of the company BASF SE, Ludwigshafen, Germany;

Aerosil®: pyrogenic silicic acid of the company Evonik Industries AG, Essen, Germany.

Method of Analysis

Unless indicated otherwise, the analytical determination of the lipolytic activity is undertaken by the so-called tributyrin assay according to Erlanson, Ch. & Borgström, B: "Tributyrine as a Substrate for Determination of Lipase Activity of Pancreatic Juice and Small Intestinal Content"; Scand. J. Gastroent. 5, 293-295 (1970). The indication of the lipolytic activity determined by the so-called tributyrin assay is undertaken synonymously in TBU units (TBU u., sometimes abbreviated to TBU), wherein the notations (with/without abbreviation point, with/without hyphen as well as with/without space) sometimes vary greatly in the scientific literature. In that, an enzymatic activity of 1 unit (1 enzyme unit) corresponds to a substance conversion of 1 μmol of substrate per minute.

The values given are normalized values, which are based on the protein content of burlulipase. The residual water content is determined according to Karl Fischer. Here, formamide is optionally used as solubilizer.

The analytical determination of the breaking strength is carried out in accordance with the relevant method of the European Pharmacopoeia—Ph. Eur. "2.9.8 Breaking strength of tablets"—with a breaking strength tester of the Schleuniger 6D type.

Example 1

Preparation of an Orodispersible Tablet

Preparation of a Solution for Freeze-Drying 26.11 parts of water, 5 parts of fish gelatin and 4 parts of mannitol are combined and heated to 60° C.±2° C. with stirring. The solution is cooled to 8° C.±2° C. and the pH value of the resulting solution is adjusted to 7.75±0.25 by adding a 3% by weight solution of sodium hydroxide in water. For that, 1.44 parts of soda lye are required. Then 63.45 parts of a burlulipase solution are added and mixed well. The burlulipase solution has a burlulipase concentration of 23.64 mg of protein/ml.

Freeze-Drying

Respectively 200 mg of the solution thus prepared are introduced into one pocket each of a blister. The pockets have the shape of tablets with a diameter of 11.50 mm and a height of 2.50 mm. Then, the blister filled with the solution is cooled to −80° C. within 3 to 4 minutes. The frozen product is then dried at 0° C. over a period of about 9 hours down to a moisture content of less than 5% by weight. The tablet thus produced contains 3 mg of burlulipase protein. After dissolution of the tablet in water, the rate of recovery of the burlulipase activity was 98.7% of the activity of the burlulipase solution originally used. At this rate of recovery, it can essentially be assumed that the losses only occur by burlulipase adhering to the devices used and that the burlulipase is practically not decomposed or deactivated. The orodispersible tablet gives an acceptable visual impression. It dissolves in 100 ml of water at 18.8° C. with stirring within 10 seconds without residue.

Example 2

Storage Stability Test

The blisters of the orodispersible tablets produced were stored at 40° C. and 75% of atmospheric humidity for 3 months. After dissolution of the tablet in water, the rate of recovery of the burlulipase activity was 96.1% of the activity of the burlulipase solution originally used. Storage at room temperature in excess of 36 months showed no change in the activity of burlulipase. These values suggest that the orodispersible tablets produced are sufficiently stable in storage for use as pharmaceutical products.

Example 3

Preparation of a Liquid Pharmaceutical Product

The tablet from a pocket of the blister is placed in 100 ml of Evian® water. The tablet dissolves without residue within 2 seconds while stirring.

Example 4

Comparative Example

Production of a tablet containing burlulipase (freeze-dried lyophilizate from in-house production) by classical tableting In this example, the analytical determination of the lipolytic activity was carried out by the relevant method of the International Pharmaceutical Federation (Fédération International Pharmaceutique, FIP) according to Demeester, J. et al.: "XI. Microbial Lipases (F.I.P)"; Drugs and the pharmaceutical sciences: 84, Pharmaceutical enzymes, 379-382 (1997). The indication of the lipolytic activity determined by this method is given in FIP units (FIP u.), wherein the notations (with/without abbreviation point, with/without hyphen as well as with/without space) sometimes vary greatly in the scientific literature.

The components 1) to 6) were mixed for 10 minutes in a Zoller free-fall mixer. After component 7) had been added, the mixture was finally mixed for another 5 minutes.

| | | |
|---|---|---|
| 1) | Burlulipase lyophilizate (lipolytic activity: 3660 FIP u./mg) | 11.02 g |
| 2) | Avicel ® PH-101 | 38.77 g |
| 3) | Emcompress ® | 42.01 g |
| 4) | Talcum Ph. Eur. | 4.67 g |
| 5) | Kollidon ® CL | 1.75 g |
| 6) | Aerosil ® | 0.78 g |
| 7) | Magnesium stearate Ph. Eur. | 1.00 g |
| | Total mass: | 100.00 g |

The resulting mass, ready to be pressed, was compressed into tablets with an average mass of 135.6 mg. For this purpose, an eccentric tablet press of type Korsch EK 0 (available from KORSCH AG, Berlin, Germany), fitted with a 7.0 mm punch (dragée-shaped), was used. The pressing pressure was 21 kN. The height of the tablets was 3.46 mm on average, the breaking strength of the tablets was 157 N on average.

The burlulipase lyophilizate (active ingredient) used has a specific lipolytic activity of 3660 FIP u./mg. Since 11.02 g are used, a total amount of burlulipase with a total lipolytic activity of approx. 40.33 million FIP u. is used. Since the total mass of the components used is 100 g, a specific activity of 403.3 FIP u./mg is thus calculated for the total mass of the components of the mixture intended for compression. After mixing, a specific lipolytic activity of 335 FIP u./mg is measured in the mass ready for pressing. Thus, a loss of lipolytic activity of 16.9% results from mixing alone. The final product, i.e. the compressed tablet, only has a specific lipolytic activity of 244 FIP u./mg. Thus, there is a further loss of the lipolytic activity of 27.2% (compared to the specific lipolytic activity of the mass ready for pressing of 335 FIP u./mg) as a result of the pressing. Accordingly, the total loss of lipolytic activity by processing a lyophilizate of burlulipase to give a tablet is 39.5% (a reduction from 403.3 FIP u./mg to 244 FIP u./mg). Since burlulipase usually is initially obtained as a liquid solution during production, there is an additional loss of activity due to lyophilization.

Thus, the rate of recovery of the burlulipase activity in the classical production of tablets by mixing and pressing is only 60.5% of the activity of the burlulipase lyophilizate originally used. In comparison to this, the rate of recovery of the burlulipase activity in the production of the orodispersible tablet according to the invention is 98.7% of the activity of the burlulipase solution initially used.

The invention claimed is:

1. An orodispersible tablet comprising amorphous burlulipase.

2. The orodispersible tablet according to claim 1, wherein said tablet comprises a lyophilizate.

3. The orodispersible tablet according to claim 1, wherein said tablet comprises a lyophilizate of a composition comprising burlulipase.

4. The orodispersible tablet according to claim 3, wherein said lyophilizate is a lyophilizate of an aqueous solution comprising burlulipase.

5. The orodispersible tablet according to claim 4, wherein said lyophilizate of an aqueous solution comprising burlulipase has been freeze-dried at a temperature of 0° C. or less.

6. The orodispersible tablet according to claim 1, wherein the tablet contains no effervescent additive and no disintegrants.

7. The orodispersible tablet according to claim 1, further comprising at least one excipient selected from the group consisting of binders and structure-forming excipients.

8. The orodispersible tablet according to claim 7, further comprising an acid or base for adjusting the pH and/or a surfactant for improving the disintegration or the dissolution behavior.

9. The orodispersible tablet according to claim 7, wherein said at least one binder comprises fish gelatin, and said at least one structure-forming excipient comprises mannitol, and further comprising sodium hydroxide.

10. The orodispersible tablet according to claim 1, wherein the tablet consists of burlulipase, fish gelatin, mannitol, sodium hydroxide and residual water.

11. The orodispersible tablet according to claim 1, wherein the tablet comprises 0.1 to 25 mg of burlulipase protein.

12. A method of preparing a liquid pharmaceutical composition comprising burlulipase, comprising the step of introducing an orodispersible tablet according to claim 1 into a liquid.

13. The method of claim 12, wherein the liquid is a beverage.

14. The method according to claim 12, wherein the composition is in the form of a solution, a suspension or an emulsion.

15. A process for producing an orodispersible tablet according to claim 4, comprising the steps of:
   providing an aqueous solution comprising the burlulipase and excipients,
   filling the aqueous solution into a mold,
   freezing the aqueous solution in the mold,
   freeze-drying the aqueous solution in the mold.

16. The orodispersible tablet according to claim 1, wherein the burlulipase activity upon solubilization is ninety-percent or greater of the activity of the solution, emulsion or suspension used to prepare the lyophilizate.

* * * * *